United States Patent
Rennebeck et al.

(10) Patent No.: US 6,468,312 B1
(45) Date of Patent: Oct. 22, 2002

(54) UREAPOIETIC ORGAN REPLACEMENT

(76) Inventors: Klaus Rennebeck, Blumenstrasse 16, D-73240 Wendlingen (DE); Albert Scheller, Albstrasse 7, D-70806 Kornwestheim (DE)

( * ) Notice: Subject to any disclaimer, the term of this patent is extended or adjusted under 35 U.S.C. 154(b) by 0 days.

(21) Appl. No.: 09/744,516
(22) PCT Filed: Jul. 26, 1999
(86) PCT No.: PCT/EP99/05317
§ 371 (c)(1), (2), (4) Date: Apr. 9, 2001
(87) PCT Pub. No.: WO00/06218
PCT Pub. Date: Feb. 10, 2000

(30) Foreign Application Priority Data

Jul. 26, 1998 (DE) .......................... 198 33 562

(51) Int. Cl.$^7$ .................................. A61F 2/02
(52) U.S. Cl. .................... 623/23.64; 435/180
(58) Field of Search ............. 623/23.64–23.66, 623/23.72–23.74; 435/180

(56) References Cited

U.S. PATENT DOCUMENTS 5,770,417 A * 6/1998 Vacanti et al. .............. 435/180
6,107,043 A * 8/2000 Jauregui et al. ................ 435/6
6,368,356 B1 * 4/2002 Zhong et al. ............ 623/23.75

* cited by examiner

Primary Examiner—David H. Willse
Assistant Examiner—Suzette J. Jackson
(74) Attorney, Agent, or Firm—Fay, Sharpe, Fagan, Minnich & McKee, LLP

(57) ABSTRACT

The invention relates to a bionic organ replacement which has a structure consisting of three groups of textile hollow microfibers. The hollow microfibers of each group run into in a liquid conductor which is central respectively. The hollow microfibers of the first group (1) are made from a proton-conducting material and have perforations (2) for draining bile into the area inside the fibers (1). One of the surfaces in essentially every hollow microfiber (1) of the first group (1) is hydrophilic and lipophilic whilst the other surface is hydrophobic and lipophobic. Cell cultures can be grown on the outer surfaces of all of the hollow microfibers.

17 Claims, 1 Drawing Sheet

UREAPOIETIC ORGAN REPLACEMENT

Figure 1:
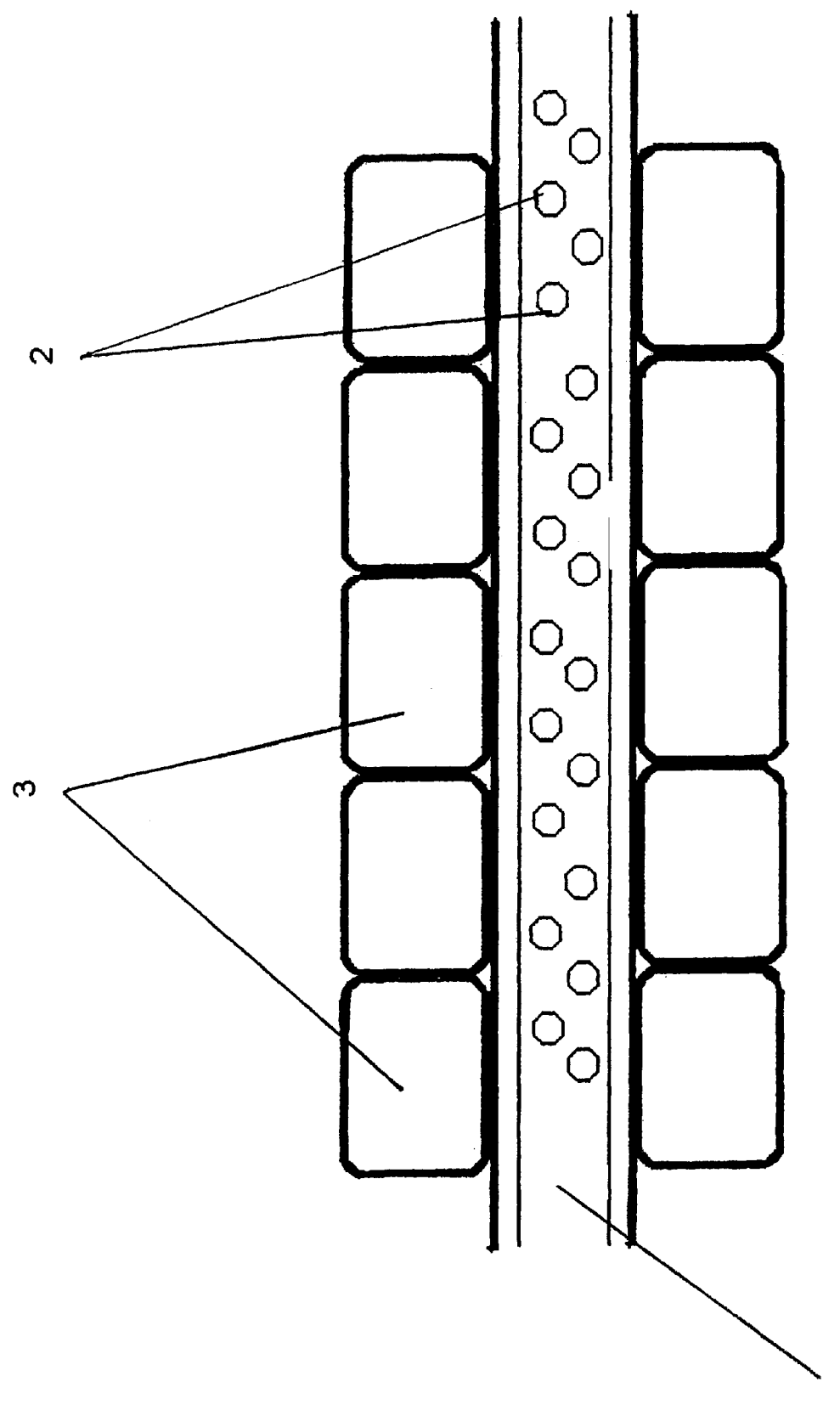

The invention relates to a bionic organ replacement, i.e. an "artificial liver" for intracorporeal as well as extracoporeal application.

It is general knowledge that different metabolic processes occur in the human liver. The digestive products are stored and processed in the hepatocytes. In addition, essential importance is attributable to the liver as a detoxification organ.

The different structures of the hepatocytes, the cytoplasm, the fine and rough endoplasmic reticulum, lycosomes, peroxisomes and the Golgi complex with mitochondria, each carrying out their respective different functions. As an example mention is made of the generation of urea, the diamide of carbon dioxide in the mitochondrial matrix of the hepatocytes. The formation of bile, i.e. bile salts and bile pigments is also part of the functions of the liver. The bile fluid which is separated by the hepatocytes as secretion is received by the interlobular gall capillaries and transmitted to the interhepatic gall ducts.

It is the object of the present invention to provide an organ replacement which is capable, in case of existing organ insufficiency or organ failure, to assume said functions, at least in part, and which is suitable for intracorporeal as well as extracorporeal application.

Said object is solved according to the invention by a ureapotetic organ replacement in accordance with claim 1.

The bionic organ replacement has a structure consisting of three groups of hollow textile micro fibers, whereby the hollow micro fibers of each group issue into at least one respectively central liquid conductors, with the hollow micro fibers of the first group being made of proton-conducting material and having perforations for drainage of bile fluid into the interior of the fibers and one of the surfaces of essentially every hollow microfiber of the first group being hydrophilic and lipophilic, whereas the other of the surfaces is hydrophobic and lipophobic, and whereby cell cultures can be grown on the outer surface of all of the hollow micro fibers.

The invention-specific organ replacement is designed in such manner that if hepatocytes are cultured on the surfaces of the hollow micro fibers, said organ replacement is capable of essentially fulfilling all functions of the liver, both intracorporeal as well as extracorporeal. The hollow micro fibers of the structure have textile properties, i.e. they are extremely fine and flexible. They form the capillary vessels of the artificial liver.

The human liver is constructed of approximately 1 to 1.5 million of liver lobules (lobuli hepati), which have a height of approximately 2 mm and a diameter of approximately 1 to 3 mm and consist of liver cells (hepatocytes) which are arranged approximately polyhedrally. The bile which is formed in the liver lobules is drained as secretion via the interlobular gall capillaries and the small gall ducts into the gall bladder (vesica fellea) or via the gall duct (ductus chlodeochus) directly into the small intestine. The interlobular gall capillaries generally have a diameter from 0.1 to 1.5 $\mu$m but can, however, in case of obstruction of the bile flow expand to approximately 15 to 20 $\mu$m.

The functions of the interlobular gall capillaries in the organ replacement according to the invention are carried out by the hollow micro fibers of the first group. They must be made of a material, the same as the natural gall capillaries, which is proton-conductive. Apatit, for example, as well as some polymers, specifically polytetrafluorethylene, have proven themselves suitable for said purpose. In order to provide the larges possible surface for culturing the cells, preference is given to spongiform hollow micro fibers. In addition, the fibers must be structured in such manner that they will selectively pass the involved metabolites, in other words, they are semi-permeable.

Another requirement consists in that one of the surfaces of each hollow micro fiber of the first group, preferably the inner surface, is lipophobic and hydrophobic and the other surface, preferably the outer surface, lipophilic and hydrophilic. In this fashion decomposition of the cells can be prevented by the bile formed in the hepatocytes. The surfaces of the hollow micro fibers can, for example, be rendered lipophobic or hydrophobic, in other words they can be "sealed" by a coating with appropriate polymers and ceramic materials. The relevant technology is known to the expert in this field and is therefore not explained in greater detail.

For purposes of draining the bile into the hollow micro fibers of the first group, these are provided with perforations of the entire wall thickness. The perforations in the hollow micro fibers are made during manufacture by means of stretching and laser application. The bile secretion enters into the hollow micro fibers of the first group via the perforations, said hollow micro fibers constituting the synthetic bile capillaries, and is passed from there to one of several fluid conductors which constitute the synthetic small gall ducts.

In addition to the capillaries and ducts for the bile, the human liver has vessel branches originating from the hepatic artery (arteria hepatica) and the portal vein (vena portae) which supply the liver lobes with blood. The surfaces of the hepatocytes are partially enclosed with cell membranes or plasma membranes which function as separation walls vis-a-vis the neighboring hepatocytes, whereby the distance amounts to approximately 100 to 200 Å. Between the star-shaped hepatocytes approaching the central vein (vena centralis) are formed so-called liver sinusoids, having a diameter equal to approximately 9 to 12 $\mu$m, in which flows the blood coming from the vessel branches to the central vein. Between the sinusoidal wall, permeable with respect to blood plasma and macromolecule, and the hepatocytes, there are so-called Disse's spaces.

According to the invention, the branches or capillaries of the human liver coming from the portal vein and the hepatic artery, are formed by the hollow micro fibers of the second and third group. These have, in accordance with the measurements of the real branches, an inner diameter of approximately 1 to 150 $\mu$m. According to the properties of the branches of the portal vein and the hepatic artery, the hollow micro fibers of the second and third group have a lower proton conductivity and act as ion- or electrolyte separation membranes.

Ceramic substances and polymers have proven themselves as materials particularly appropriate for said purpose. The hollow micro fibers of the second and third group respectively issue in a central fluid conductor, the synthetic portal vein or the synthetic hepatic artery. They can be made of bio-compatible material customarily employed for artificial vessels.

On the organ replacement according to the invention, a culture of human liver cells is grown, preferably in vitro, until the outer surface of the hollow micro fibers is fully overgrown with human liver cells. The liver cells or hepatocytes have in their center the nucleus. In addition, the liver cells have the so-called mitochondria, which are equipped with multi-semipermeable membranes with a cut-off accuracy in the micro-, ultra- or nano-range, with size and load exclusion, or a combination of both, and in which, among others, enzymatic reactions occur for the supply of energy.

Finally, the Golgi apparatuses are located in the liver cells in sequences, in whose so-called cisterns, lipids can occur.

As soon as sufficient cell growth exists, the organ replacement according to the invention can be surgically inserted into the body under application of immuno-therapeutics. It is hereby possible to introduce the medicaments into the interior of the hollow micro fibers. Needless to say, the artificial liver according to the invention can also be used as an extracorporeal organ replacement.

Insertion of the organ replacement into the human body is a fundamentally possible alternative to the in vitro cell culture growth, so that still healthy liver cells grow incorporeally over the hollow micro fiber structure. Said method of procedure is specifically advisable with only partial liver damage and can, perhaps, be done endoscopically.

The hollow micro fibers of the organ replacement according to the invention have an inner diameter of approximately 0.1 to 50 $\mu$m. This corresponds to the inner diameter of the natural vessels. In principle, if needed, artificial vessel with different measurements can be used, provided this is logical and technically executable. Hollow micro fibers of said diameter can be produced, for example, via spinning process. Relative to the details of the properties, the possible raw materials and the manufacturing method, reference is made to the International Application WO97/26225. As is apparent from this publication, the hollow micro fibers of the specified dimensions can be produced with high precision. It is thus possible to keep the variations of diameter and wall thickness of the hollow micro fibers within a range of plus/minus 6% as a result of which uniform structure can be guaranteed.

The hollow micro fibers are preferably arranged in a cross-sectional honey-comb shaped structure. This corresponds, in turn, to the natural structure of the tissue framework around the individual liver lobules. In general, it can be stated that the structure of the hollow micro fibers and appropriate fluid conductors should be adapted, to the extent possible, to the natural structure of the corresponding vessels in order to obtain maximum compatibility with incorporeal use of the invention-specific organ replacement. As an alternative to the honey-comb structure, corrugated cardboard shape arrangement is also conceivable or any other structure which results in maximum surface of cell overgrowth. The size of a honeycomb cell or a corrugated cardboard structure cell preferably corresponds to approximately the size of a human liver lobule.

The bile flows of the liver consist of approximately 97% water, 0.7% bile salt, 0.2% bile pigments, 0.06% cholesterol, 0.7% inorganic salts, 1% fatty acids, lecithin and 0.1% fat. The metabolism of the liver is determined by the activity of the human being, by the basic energy need as well as by the food supply. On average, approximately 600 ml bile fluid are generated each day. For that reason, the number and size of the perforations is preferably designed in such fashion so that the resulting bile flow amounts to approximately 100 to 3000 ml per day. Naturally, the design may also call for a lower amount of bile fluid, for example if the invention-specific organ replacement is to substitute only a portion of the human liver. As a rule, a diameter of perforations have proven adequate which is approximately equal to the diameter of the filament lumen of the hollow micro fiber, whereby the total area of perforations should be about 30% if fiber surface.

The hollow micro fibers preferably have a delayed degradation capability and are adjustably degradable. As a result, the service life of the hollow micro fibers can be adapted to the age of the person whose liver is to be substituted by the organ replacement according to the invention.

According to a particularly preferred specific embodiment, the organ replacement according to the invention comprises a porto-caval shunt. This has the benefit of redundancy.

Similarly, the fluid conductors corresponding to the portal vein or the hepatic vein may be designed with a shut-off organ. Construction, manufacture and attachment of such shut-off organs or shunts in artificial vessels are known in the state of the art, for reasons of which the pertinent details are not discussed herein more specifically.

The invention-specific organ replacement can be produced in any selected size, in other words a complete liver as well as only a part of same can be substituted by the organ replacement. The artificial organ according to the invention is preferably operated as integral solid foundation reactor with a blood dwelling time of approximately 5 to 250 minutes, whereby occurrence of hemostatis can largely be excluded by the properties of the hollow micro fibers, in particular based on their textile properties. With use of extracorporeal application of the invention-specific organ replacement, it is possible to select a dialysis-corresponding treatment method. In the following, the invention is described with respect to the attached drawing—but is not limited to said embodiment—and its sole figure represents a cross-section through a hollow micro fiber 1 of the first group, constituting a synthetic interlobular gall capillary. The hollow micro fiber 1 is made of spongy material which permits excellent cell growth. In the walls of the hollow microfiber 1 are inserted perforations or punchings 2, which serve for drainage of bile fluid into the lumen of the hollow micro fiber. The bile flow is beneficially affected by the lipophilic and hydrophilic nature of the outer surface of the hollow micro fibers as well as by the lipophobic and hydrophobic quality of the inner surface of same.

The liver lobules 3 comprising the liver cells are schematically indicated on the fiber. The bile fluid which has entered into the hollow micro fibers 1 through the perforations 2 is further transported to the small biliary ducts (not shown in the Fig.) from where is gets into the gall bladder or via the biliary duct directly into the small intestine if the invention-specific organ replacement is located within the human body.

An artificial liver is created by the described bile drainage system, with said artificial liver being capable of employment outside as well as inside the body, since the bile fluid does not decompose the liver cells. Thus an organ replacement is provided which is adapted, to the extent possible, to the natural structure and function of the human liver.

The hollow micro fibers 1 of the first group, which constitute the synthetic interlobular bile capillaries are interlinked in such fashion with the hollow micro fibers of the second and third group that a structure is created around each liver lobule replicating the natural capillary network. To that end, the hollow micro fibers can be designed either as tissue or as spun fleece or as tension bond.

It should be noted that in case the term "human liver" is used in the preceding, this need not be interpreted in the restrictive sense of the word, and that the utilization of the invention-specific organ replacement is not at all limited to humans alone, but can extend as well to animals with similar liver construction. Needless to say, in such case potential modifications must be made with respect to size and/or structure of the organ replacement according to the invention. To that end, the general principle can be established that the organ replacement should be adapted, to the extent possible, to the actual conditions of the to be substituted organ.

What is claimed is:

1. Bionic organ replacement, presenting a structure of three groups of textile hollow micro fibers, whereby the hollow micro fibers of each group issue into a respectively central liquid conductor, wherein the hollow micro fibers (1) of the first group are made of proton-conducting material and present perforations (2) for the drainage of bile liquid into the interior of the fibers (1) and the one of the surfaces of essentially each hollow micro fiber (1) of the first group is hydrophilic and lipophilic, while the other of the surfaces is hydrophobic and lipophobic and, wherein cell cultures can be grown on the outer surfaces of all of the hollow micro fibers.

2. Bionic organ replacement, comprising a structure of three groups of textile hollow micro fibers, whereby the hollow micro fibers of each group issue into a respectively central liquid conductor, whereby cell cultures can be grown of the outer surfaces of all of the hollow micro fibers, characterized in that the hollow micro fibers (1) of the first group are made of proton-conductive material and present perforations (2) for the drainage of bile liquid into the interior of the fibers (1) and the surfaces-of essentially each hollow micro fiber (1) of the first group are hydrophilic and lipophilic, while the other of the surfaces is hydrophobic and lipophobic.

3. Bionic organ replacement according to claim 2, characterized in that the outer surfaces of the hollow micro fibers are fully overgrown with human liver cells, cultured in vitro.

4. Bionic organ replacement according to claim 3, characterized in that the hollow micro fibers have an inner diameter of approximately 0.1 to 50 μm.

5. Bionic organ replacement according to claim 3, characterized in that the hollow micro fibers are arranged, in cross-section, in a honey-comb shaped structure.

6. Bionic organ replacement according to claim 3, characterized in that the liquid conductor is compatible with the structure of the corresponding human vessel.

7. Bionic organ replacement according to claim 3, characterized in that the number and size of the perforations (2) is designed in such manner that a bile flow is possible of approximately 100 to 3000 ml/d.

8. Bionic organ replacement according to claim 2, characterized in that the hollow micro fibers have an inner diameter of approximately 0.1 to 50 μm.

9. Bionic organ replacement according to claim 8, characterized in that the hollow micro fibers are arranged, in cross-section, in a honey-comb shaped structure.

10. Bionic organ replacement according to claim 8, characterized in that the liquid conductor is compatible with the structure of the corresponding human vessel.

11. Bionic organ replacement according to claim 8, characterized in that the number and size of the perforations (2) is designed in such manner that a bile flow is possible of approximately 100 to 3000 ml/d.

12. Bionic organ replacement according to claim 2, characterized in that the hollow micro fibers are arranged, in cross-section, in a honey-comb shaped structure.

13. Bionic organ replacement according to claim 12, characterized in that the liquid conductor is compatible with the structure of the corresponding human vessel.

14. Bionic organ replacement according to claim 12, characterized in that the number and size of the perforations (2) is designed in such manner that a bile flow is possible of approximately 100 to 3000 ml/d.

15. Bionic organ replacement according to claim 2, characterized in that the liquid conductor is compatible with the structure of the corresponding human vessel.

16. Bionic organ replacement according to claim 15, characterized in that the number and size of the perforations (2) is designed in such manner that a bile flow is possible of approximately 100 to 3000 ml/d.

17. Bionic organ replacement according to claim 2, characterized in that the number and size of the perforations (2) is designed in such manner that a bile flow is possible of approximately 100 to 3000 ml/d.

* * * * *